United States Patent [19]

Pimblett

[11] Patent Number: 5,258,549
[45] Date of Patent: Nov. 2, 1993

[54] PROCESS FOR PREPARING CARBOXYLIC ACIDS

[75] Inventor: Gillian Pimblett, Pocklington, England

[73] Assignee: BP Chemicals Limited, London, England

[21] Appl. No.: 326,364

[22] Filed: Mar. 21, 1989

[30] Foreign Application Priority Data

Mar. 26, 1988 [GB] United Kingdom ............... 8807284

[51] Int. Cl.$^5$ ............................................ C07C 51/12
[52] U.S. Cl. ................................................ 562/519
[58] Field of Search .................... 562/519; 260/413

[56] References Cited

U.S. PATENT DOCUMENTS

| | | | |
|---|---|---|---|
| 2,650,245 | 8/1953 | Thomas et al. | 562/519 |
| 2,650,246 | 8/1953 | Thomas et al. | 562/519 |
| 3,769,329 | 10/1973 | Paulik et al. | 562/519 X |
| 4,328,125 | 5/1982 | Drago et al. | 252/426 |
| 4,426,537 | 1/1984 | Gauthier-Lafaye et al. | 562/519 |

FOREIGN PATENT DOCUMENTS

| | | | |
|---|---|---|---|
| 0069514 | 1/1983 | European Pat. Off. | |
| 90443 | 10/1983 | European Pat. Off. | 562/519 |
| 130582 | 6/1984 | European Pat. Off. | |
| 120631 | 10/1984 | European Pat. Off. | 562/519 |
| 1966695 | 8/1969 | Fed. Rep. of Germany | |
| 1233121 | 5/1971 | United Kingdom | |
| 1277242 | 6/1972 | United Kingdom | |
| 2089803 | 6/1982 | United Kingdom | |

OTHER PUBLICATIONS

Catalytic Features of Carbon Supported Catalysts, ACS, Series, 328, 1987.
Chemistry Letters, 1987, 895.
Ind. Chem. Prod. Res. Dev., 1983, 22, 436.
Ind. Chem. Prod. Res. Dev., 1982, 21, 429 Journal of Catalysis 59, 53–60 (1979).

*Primary Examiner*—José G. Dees
*Assistant Examiner*—Joseph M. Conrad
*Attorney, Agent, or Firm*—Brooks Haidt Haffner & Delahunty

[57] ABSTRACT

A process for preparing carboxylic acids (e.g. acetic acid) from alcohols (e.g. methanol) by carbonylation is provided. The process employs a catalyst comprising rhodium and nickel supported upon a carbon, preferably a high surface area carbon. The process described is carried out in the presence of hydrogen and a halide promoter leading to high yields of the carboxylic acid under very mild conditions (1 to 50 atmospheres, 150°–300° C.).

6 Claims, No Drawings

PROCESS FOR PREPARING CARBOXYLIC ACIDS

The present invention relates in general to the production of carboxylic acids and in particular to a process for the production from an alcohol having n carbon atoms of a carboxylic acid having n+1 carbon atoms by carbonylation of the alcohol in the presence of a heterogeneous catalyst. In a preferred embodiment of the invention acetic acid is produced by the carbonylation of methanol.

The carbonylation of methanol has been known for a long time. As long ago as 1953 Reppe disclosed in Justus Liebig's Ann. Chem., 1953, 582, 1 that the carbonyls of iron, cobalt and nickel catalyse methanol carbonylation to acetic acid at temperatures of 250° to 270° C. and pressures in the range from 200 to 350 bar in the presence of halide promoters.

Halcon have since reported that the carbonylation of methanol is catalysed by a nickel acetate/tetraphenyltin/methyl iodide system under relatively mild conditions (35 bar and 150° C.) and other patents have disclosed that nickel carbonyl or nickel compounds are effective catalysts in the presence of iodide at pressures as low as 30 bar when organic amines or phosphines are incorporated in the liquid reaction media. Halcon in their publications maintain that hydrogen stabilises the catalysts. Recently, in GB-A-2089803 it has been disclosed that molybdenum and tungsten promoted nickel catalysts promoted with trivalent organo-phosphorus or organo-nitrogen and iodide give high yields of acetic acid from methanol in the liquid phase (33 bar, 188° C.). Again, hydrogen reportedly does not hinder the reaction and may stabilise the catalyst. Reference is also made to the possibility of vapour phase operation using supported catalyst components. Halcon have also disclosed in DE-A-3335595 the high yield production of acetic acid from methanol/methyl acetate using molybdenum/nickel/lithium iodide/iodide catalyst components at pressures of 83 bar. Lanthanum salts have been shown in U.S. Pat. No. 4,426,537 to be efficient promoters of nickel catalysts in the liquid phase. Finally, it is well-known from Monsanto patents that carbonyl complexes of rhodium are very active for methanol carbonylation in the presence of iodide promoters under very mild conditions (35 bar, 180° C.). The conclusions to be reached from the foregoing are that both nickel and rhodium catalysts are known to be active for the homogeneous liquid phase carbonylation of methanol under milder conditions than those reported by Reppe and that using nickel catalyst the presence of hydrogen can be tolerated and may sometimes have a beneficial effect in terms of stabilising the catalyst. However, for a number of reasons including elimination of catalyst separation and recycle problems, there is a preference for operation in the vapour phase using a heterogeneous catalyst.

A number of supported nickel catalysts have been reported for the vapour phase reaction. High methanol conversions to acetyls on activated carbon supports at temperatures of between 202° and 345° C. and pressures of about 14 Kg $cm^{-2}$ are reported in EP-A-0069514 (Toyo Engineering). A large amount of hydrogen in the carbon monoxide feed is said to be undesirable, however. In DE-A-3,323,654 it is reported that nickel on activated carbon together with promoters such as palladium and palladium/copper are reasonably active catalysts at temperatures of between 280° and 310° C. for methanol carbonylation. Fujimoto et al have studied nickel on activated carbon extensively, reporting on metal loadings and reaction conditions (Ind. Chem. Prod. Res. Dev., 1983, 22, 436; ibid 1982, 21, 429), on the features of nickel on the carbon support (Catalytic Features of Carbon Supported Catalysts, ACS Series, 328, 1987) and the increase in activity and production of acetic acid as hydrogen is introduced into the gas feed (Chemistry Letters, 1987, 895).

Supported rhodium catalysts have also been extensively studied. Zeolite supports have been shown to be effective catalysts both for the Y-form (J. Catalysis, 1979, 59, 53) and for the Na-X zeolite with [Rh(NH$_3$)$_5$Cl]Cl$_2$ where the rate was found to be similar to that of the homogeneous reaction. The metal carbonyls $M_n(CO)_m(X)_p{}^{-2}$ [where M=Rh, Co, Ru, Os, Ir or Fe; x=anion, halide, hydride or alkyl] bound to an anion exchange resin containing quaternary ammonium salts have also been shown to be effective carbonylation catalysts in U.S. Pat. No. 4,328,125.

Similarly, matrix bound rhodium (I) complexes formed by ligand exchange of RhCl(CO)(PPh$_3$)$_2$ with styrene divinylbenzene copolymer have been shown by Jarrel et al in J. Catalysis, 1975, 40, 255 to be active towards carbonylation, albeit at low conversions (20%) under mild conditions (20 barg, 95° C.). Monsanto have investigated a very large number of modifiers (metals from Groups IB, IIIB, IVB, VB, VIB, VIII and the lanthanides and actinides) on supported rhodium catalysts. The supports are mainly activated carbons and process conditions are generally low pressures (1 atmosphere), see for example U.S. Pat. No. 3,717,670; EP 120631; GB-A-1,233,121 and GB-A-1,277,242. Nickel is mentioned as a modifier (U.S. Pat. No. 3,717,670 and 1,277,242) but no emphasis is placed upon its use and no activation by hydrogen is mentioned. It is concluded that the use of supported rhodium catalysts is well-known and that nickel has been used as a modifier therefor, though no activation effect of hydrogen has been observed with either rhodium alone or rhodium/nickel-containing catalysts. Hydrogen is said to activate supported nickel catalysts in some prior art disclosures, for example Fujimoto et al in Ind. Chem. Prod. Res. Dev. referred to hereinbefore, whereas in others, for example EP-A-0069514, significant amounts of hydrogen are said to be detrimental.

We have now found that certain carbon-supported rhodium catalysts are active for the conversion of methanol to acetic acid using mixtures of carbon monoxide and hydrogen under very mild operating conditions.

Accordingly the present invention provides a process for the production from an alcohol having n carbon atoms of a carboxylic acid having n+1 carbon atoms which process comprises contacting at elevated temperature and pressure the alcohol with a gaseous mixture of carbon monoxide and hydrogen in the presence of a catalyst comprising rhodium and nickel supported on a carbon support and a halogen or halogen compound promoter.

As regards the alcohol having n carbon atoms, this may suitably be an aliphatic alcohol having from 1 to 12 carbon atoms including methanol, ethanol, propanol and isopropanol, butanols, pentanols and hexanols, and also the higher alcohols such as the decanols, including isomeric forms thereof. A preferred alcohol is methanol, from which there is obtained acetic acid. The methanol may be essentially pure or may contain impurities commonly associated therewith, for example water and ethanol. Polyhydric alcohols may be used, as may also aromatic hydroxyl-containing compounds, for example phenol.

The alcohol is contacted with a gaseous mixture of carbon monoxide and hydrogen, which may be fed separately or pre-mixed. However, it is an advantage of the process of the present invention that gaseous mixtures of carbon monoxide and hydrogen obtainable by such processes as the steam reforming or partial oxidation of methane-containing gaseous mixtures may be used, with or without adjustment of the carbon monoxide to hydrogen molar ratio. In the commercial production of acetic acid by carbonylation of methanol the carbon monoxide is produced in admixture with hydrogen and thereafter the carbon monoxide is separated from the hydrogen for use in the carbonylation. The facility to use mixtures therefore represents a considerable economic benefit by eliminating the separation step. Such mixtures may contain small amounts of impurities, such as methane, nitrogen and carbon dioxide, which can be tolerated in the process of the invention. The carbon monoxide may comprise from 1 to 95% by volume of hydrogen. Preferably the hydrogen content of the carbon monoxide is such that the carbon monoxide to hydrogen molar ratio is in the range 10:1 to 1:4.

It is a feature of the present invention that the catalyst comprises both rhodium and nickel upon a carbon support. There appears to be an unexpected synergistic effect when rhodium and nickel are used together in the presence of hydrogen. In particular, the activity of catalysts having both rhodium and nickel present is greater than the individual contributions of the nickel and the rhodium. Thus, carbon-supported nickel/rhodium catalysts can exhibit high activity and selectivity, for example the conversion of methanol to acetic acid under very mild operating conditions.

Whilst the actual form of the metals during the reaction is not known with certainty, it is believed that the metals may be at least partially carbonylated. It is therefore possible to use the metals in elemental form or in the form of a compound, for example a salt, thereof. As the carbon support there may suitably be used any activated or unactivated high surface area carbon or high surface area graphite. Preferred supports are the high surface area activated carbons. Examples of such materials are high surface area carbons having a surface area in excess of 500 $m^2g^{-1}$.

The catalyst may suitably be prepared by impregnating the support with a solution or solutions, suitably aqueous, of a soluble compound, for example a salt, of the metals, removing the solvent and drying the composition so-obtained. Before use in the process of the invention it is preferred to activate the catalyst, suitably by contact with a reducing gas, for example hydrogen, at elevated temperature, suitably in the range from about 100° to 650° C., typically about 400° C.

The catalyst may suitably comprise from 0.05 to 10% by weight nickel and from 0.1 to 7% rhodium. The nickel to rhodium weight ratio may suitably be in the range from 0.05:1 to 10:1.

As the promoter there is used either a halogen or a halogen compound, which may be for example a hydrogen halide, an alkyl or aryl halide, a metal halide or an ammonium, phosphonium, arsonium or stibonium halide. Promoters containing iodine as the halogen moiety are preferred. Preferably the promoter is an alkyl iodide, for example methyl iodide.

The process is operated at elevated temperature and pressure. Suitably, the temperature may be in the range from 150° to 300° C. and the pressure may be in the range from 1 to 50 atmospheres.

The process may be operated either batchwise or continuously, preferably continuously and the alcohol may be in the liquid or vapour phase. The Liquid Hourly Space Velocity for continuous operation may suitably be in the range from 0.1 to 5 and the gas to liquid vapour ratio may suitably be in the range from 1:5 to 100:1, though higher and lower ratios may be employed.

The process of the invention will now be further illustrated by reference to the following Examples and Comparison Tests.

EXAMPLE A—CATALYST PREPARATION

The activated carbon used as the support in the preparation of the catalyst was a highly microporous carbon, commercially available (ex Sutcliffe Speakman; AC 610). It has a BET surface area of 1600–1800 $m^2/g^{-1}$, a micropore volume of 0.74 $cm^3 g^{-1}$ and a total pore volume of 0.82 $cm^3 g^{-1}$.

(i) Nickel/rhodium/activated carbon catalysts were prepared by impregnating the aforementioned activated carbon with an aqueous solution of nickel nitrate and drying at 110° C. for 24 hours in an air oven. The catalyst was then activated at 400° C. for 3 hours under a stream of hydrogen, then cooled and passified with nitrogen containing trace oxygen and water impurities. Rhodium in the form of rhodium nitrate solution was then impregnated on to the material so-obtained and the catalyst was dried at 110° C. for 24 hours in an air oven. The catalyst was activated in situ at 280° C. for 1 hour under a stream of hydrogen at atmospheric pressure prior to use.

(ii) The nickel on activated carbon catalyst was prepared as for (i) above except that the rhodium impregnation step was omitted.

(iii) The rhodium on activated carbon catalyst was prepared in the manner of (i) above except that the nickel impregnation step was omitted.

EXAMPLE 1

A fixed catalyst bed flow type reactor under pressurised conditions was employed. Methanol and methyl iodide were mixed and fed with a pressure pump, contacted with hot inlet gas in a preheater furnace and then the mixed vapours were fed over a 2 ml catalyst bed in the reactor furnace. The products were then fed through a pressure reduction valve and into an on-line gas chromatograph.

The catalyst (2.5% b.w. Ni/1% b.w. Rh) (2 ml; 0.836 g) was placed in the reactor tube. The catalyst was activated in situ prior to use in the reaction at 280° C. under a stream of hydrogen (GHSV 2, 400 $h^{-1}$) for 1 hour. The reactor tube was then cooled to 180° C. and the reactants added. At a gas feed ratio of 1:2 $CO:H_2$, total pressure 9 barg, LHSV=1, gas feed:methanol:methyl iodide ratio of 100:19:1 and a bed temperature of 188° C. the conversions shown in Table 1 were obtained.

COMPARISON TEST 1

Example 1 was repeated except that a 2.5% Ni on activated carbon catalyst was employed instead of the 2.5% Ni/1% Rh/activated carbon catalyst. The conversions obtained are shown in Table 1.

COMPARISON TEST 2

Example 1 was repeated except that a 1% Rh on activated carbon catalyst was employed instead of the 2.5% Ni/1% Rh/activated carbon catalyst. The conversions obtained are shown in Table 1.

Comparison Tests 1 and 2 are not according to the invention because the catalysts lack an essential component. They are included only for the purpose of comparison.

TABLE 1

| Example | Catalyst | CO:$H_2$ | $CH_4$ | $Me_2O$ | MeOAc | AcOH | $Me_2CO$ | Total |
|---|---|---|---|---|---|---|---|---|
| 1 | 2.5% Ni/1% Rh/ activated carbon | 1:2 | 7.5 | 0 | 3.2 | 79.7 | 2.4 | 92.8 |
| CT 1 | 2.5% Ni/activated carbon | 1:2 | 4.3 | 3.3 | 4.1 | 0 | 0 | 11.7 |
| CT 2 | 1% Rh/activated carbon | 1:2 | 10.5 | 2.0 | 33.7 | 8.2 | 0 | 54.4 |

Methanol conversion (%) to:-

The results reported in the Table demonstrate that the activated carbon supported Ni/Rh catalyst is very active under mild conditions for methanol carbonylation to acetic acid. They also show that a synergistic effect exists between Rh and Ni since the activity of the bimetallic catalyst does not equate with the combined activities of the individual catalysts. The synergy acts to lower methane production and increase the selectivity to acetic acid relative to the combined activities of the individual metal catalysts.

EXAMPLES 3 and 4

Example 1 was repeated except that the proportion of hydrogen in the gaseous feed was varied. The results obtained are given in Table 2.

COMPARISON TEST 3

Example 1 was repeated except that hydrogen was omitted from the feed. The results obtained are given in Table 2.

This is not an example according to the present invention because hydrogen was absent. It is included only for the purpose of comparison.

TABLE 2

| Example | CO:$H_2$ Ratio | $CH_4$ | $Me_2O$ | MeOAc | AcOH | $Me_2CO$ | Total |
|---|---|---|---|---|---|---|---|
| CT 3 | 1:0 | 0.3 | 2.0 | 30.7 | 28.8 | 0.5 | 62.4 |
| 3 | 4:1 | 3.7 | 0 | 6.4 | 76.9 | 2.9 | 89.9 |
| 4 | 2:1 | 4.4 | 0 | 3.4 | 79.3 | 4.2 | 91.3 |
| 1 | 1:2 | 7.5 | 0 | 3.2 | 79.7 | 2.4 | 92.8 |

Methanol Conversion (%) to:-

It would appear from the results reported in Table 2 that hydrogen activates the rhodium-containing catalyst to acetic acid production without appreciable change in selectivity to methane.

COMPARISON TESTS 4 AND 5 AND 6

Comparison EXAMPLE 2 was repeated using different proportions of hydrogen in the gaseous feed. The results are reported in Table 3.

Comparison Test 4 is not an example according to the present invention because hydrogen was absent. It is included only for the purpose of comparison.

TABLE 3

| Example | CO:$H_2$ Ratio | $CH_4$ | $Me_2O$ | MeOAc | AcOH | $Me_2CO$ | Total |
|---|---|---|---|---|---|---|---|
| CT 4 | 1:0 | 4.8 | 0 | 33.4 | 7.9 | 1.3 | 47.4 |
| CT 5 | 4:1 | 7.1 | 0 | 34.1 | 19.2 | 1.6 | 62.1 |
| CT 6 | 2:1 | 6.4 | 1.6 | 36.5 | 10.7 | 0.6 | 55.3 |
| CT 2 | 1:2 | 10.5 | 2.0 | 33.7 | 8.2 | 0 | 54.4 |

Methanol Conversion (%) to:-

It can be seen from the results reported in Table 3 that hydrogen does activate the rhodium/activated carbon catalyst but not to the extent observed with the nickel/rhodium/activated carbon catalyst, and with particularly less satisfactory results at 1:2 CO:$H_2$.

I claim:

1. A vapor phase process for the production from an alcohol having n carbon atoms of a carboxylic acid having n+1 carbon atoms which process comprises contacting at elevated temperature and pressure a gaseous mixture of the alcohol, carbon monoxide and hydrogen in the presence of a catalyst comprising rhodium and nickel supported on a carbon support and a halogen or halogen compound promoter and wherein the carbon monoxide to hydrogen molar ratio in the gaseous mixture is in the ragne 4:1 to 1:2.

2. A process as claimed in claim 1 wherein the catalyst is one having a nickel to rhodium weight ratio in the range 0.25:1 to 10:1.

3. A process as claimed in either claim 1 or claim 2 wherein the catalyst contains from 0.1 to 10% by weight nickel.

4. A process as claimed in claim 1 or claim 2 wherein the catalyst contains from 0.5 to 7% rhodium.

5. A process as claimed in claim 1, wherein the alcohol having n carbon atoms is methanol and the carboxylic acid having n+1 carbon atoms is acetic acid.

6. A process as claimed in claim 1 carried out at a temperature in the range 150° to 300° C. and at a pressure in the range 1 to 50 atmospheres.

* * * * *